United States Patent [19]

Ammende et al.

[11] Patent Number: 4,976,991
[45] Date of Patent: Dec. 11, 1990

[54] METHOD FOR MAKING A SENSOR FOR MONITORING HYDROGEN CONCENTRATIONS IN GASES

[75] Inventors: Sonya Ammende, Frankfurt am Main; Hartmut Erdmann, Steinbach; Heinz-Werner Etzkorn, Neu Anspach; Klaus Zucholl, Mannheim, all of Fed. Rep. of Germany

[73] Assignee: Battelle-Institut e.V., Frankfurt am Main, Fed. Rep. of Germany

[21] Appl. No.: 426,276

[22] Filed: Oct. 25, 1989

Related U.S. Application Data

[62] Division of Ser. No. 124,326, Nov. 23, 1987.

[51] Int. Cl.$^5$ ................. G01N 27/47; B05D 5/12
[52] U.S. Cl. ........................... 427/125; 204/424; 204/429; 264/60; 427/58; 427/126.2; 427/126.3; 427/126.5
[58] Field of Search ............... 204/15, 421–429; 264/56, 60; 427/58, 125, 126.2, 126.3, 126.5

[56] References Cited

U.S. PATENT DOCUMENTS

| 3,475,223 | 10/1969 | Kummer et al. |
| 3,825,482 | 7/1974 | Wechter et al. |
| 3,843,400 | 10/1974 | Radford et al. |
| 4,024,036 | 5/1977 | Nakamura et al. |
| 4,049,891 | 9/1977 | Hong et al. |
| 4,111,777 | 9/1978 | Dobson et al. |
| 4,166,009 | 8/1979 | Fray |
| 4,272,350 | 6/1981 | Croset et al. |
| 4,377,460 | 3/1983 | Hirayama et al. |
| 4,689,122 | 8/1987 | Polak et al. |

OTHER PUBLICATIONS

A. P. Khomyakov et al., "X-Ray Diffraction Study", Chemical Abstract, vol. 86, Abstract #99364g.
N. A. Nosyrev et al., "Crystal Structure of Synthetic Khibinskite", Chemical Abstract, vol. 86, Abstract #64045b.
P. Colomban et al., "New Protonic Conductors for Hydrogen Sensors", Chemical Abstract, vol. 100, Abstract #78015m.
M. Arima et al., "Stability of Wadeite", Chemical Abstract, vol. 93, Abstract #75943p.
V. A. Kolesova et al., "Cesium Analog of Wadeite", Chemical Abstract, vol. 92, Abstract #139893m.
N. Kinomura et al., "Crystal Structure of Phases", Chemical Abstract, vol. 90, Abstract #58172g.
V. A. Blinov et al., "Refinement of the Crystal Structure of Wadeite", Chemical Abstract, vol. 86, Abstract #149059j.
J. P. Hilger, "Formation Mechanism of Wadeite", Chemical Abstract, vol. 102, Abstract #83258p.
V. N. Rudenko et al., "Crystal Structure of Sn-wadeite", Chemical Abstract, vol. 100, Abstract #124239n.
P. Colomban et al., "New Protonic Conductors for Hydrogen Sensors", Chemical Abstract, vol. 100, Abstract #78015m.
M. G. Gorskaya et al., "Refinement of Crystal Structure of Titanium Wadeite", Chemical Abstract, vol. 97, Abstract #41678y.
A. P. Khomyakov, "Separation of Mineral Species and Varieties in the Keldyshite Group", Chemical Abstract, vol. 89, Abstract #27698h.
Ph. Colomban, H. Perthius, G. Velasco, "New Protonic Conductors for Hydrogen Sensors: The Thick Film Route", pp. 375 to 391.
U. von Alpen, M. F. Bell; H. H. Hoefer, S. Schindler, "Hochtemperatur-Hochenergiezelle mit Festelektrolyt", May 1983.
Steen Yde-Andersen et al., "Properties of Nasicon Electrolytes Prepared from Alkoxide Derived Gels", Solid State Ionics, 14, pp. 73–79, (1984).

*Primary Examiner*—T. Tung
*Attorney, Agent, or Firm*—Spencer & Frank

[57] ABSTRACT

A sensor for monitoring hydrogen concentrations in gases, containing a solid electrolyte body, a detector electrode having a surface which is exposable to a gas to be monitored, and a reference electrode, in which the reference and detector electrodes make contact with the solid electrolyte, and the detector electrode contains a platinum metal or a platinum metal oxide. A method of making the sensor is also disclosed.

11 Claims, 3 Drawing Sheets

METHOD FOR MAKING A SENSOR FOR MONITORING HYDROGEN CONCENTRATIONS IN GASES

This is a division of application Ser. No. 124,326 filed Nov. 23, 1987.

BACKGROUND OF THE INVENTION

The present invention relates to a sensor for monitoring hydrogen concentrations in gases.

Hydrogen sensors are known. They generally operate with semiconductive oxides. Their drawbacks are that the semiconductive oxides must be heated to a temperature of several hundred degrees Celsius, that the response time of the sensor is very long and that they have a high cross-sensitivity for other gases.

SUMMARY OF THE INVENTION

It is an object of the present invention to provide a sensor for monitoring hydrogen concentrations in gases which can be manufactured very economically and is distinguished, in particular, by a very short response time for the hydrogen to be detected, connected with the lowest possible cross-sensitivity for other gases that need not be detected.

The solution of this problem provided by the invention is characterized in that a solid electrolyte is provided which is in contact with a detector electrode made of one of the platinum metals or their oxides and exposed to the gas to be monitored and with a reference electrode.

If a hydrogen-containing gas flows around the detector electrode, the hydrogen reacts electrochemically with the sensor. The electrical potential or change in potential, produced at the electrodes, can be evaluated and further processed by a subsequently connected electronic system. The invention thus utilizes the fact that the hydrogen contained in the gas being monitored chemically reacts at the detector electrode and thus generates an electromotive force in the sensor which produces the detector signal.

Nasicon, titsicon, khibinskite, wadeite (these compounds are described in S. Yde Andersen, J. S. Lundsgaard, C. Moller, J. Engell, *Solid State Ionics* 14 (1984) 73-79; H. von Alpen, M. F. Bell, H. H. Hoefer, S. Schindler, *Forschungsbericht T* 83-095 (1983), Bundesministerium für Forschung und Technologie; and Ph. Colomban, H. Perthuis, G. Valasco, *Proc. of the Hindsgave Workshop on Solid State Protonic Conductors for Fuel Cells and Sensors*, Sept. 5-10, 1987, pp. 377 ff. Jensen, Goodenough eds.) or $\beta$-$Al_2O_3$ are particularly suitable as solid electrolytes. The solid electrolyte includes at least one of these compounds.

One important feature of the invention is that the solid electrolyte and the electrodes are applied to a substrate in thick-film technology. With this technology, the sensor according to the invention can be produced in large numbers and very cost-effectively. However, other manufacturing methods are also possible and suitable, for example the vapor-deposition process.

Preferred is a sensor which is covered and sealed with glass, plastic or some other suitable material in such a way that at least part of the surface of the detector electrode remains exposed. The cover need cover only the top side of the sensor if its underside is covered by the substrate.

It is also of advantage for the detector electrode to be formed of platinum, palladium or palladium oxide. Palladium has the greatest hydrogen permeability of the platinum metals and thus the sensor becomes highly selective. Additionally, it is of advantage for the reference electrode to be manufactured of materials exhibiting stable sodium ion activity and the reference electrode to be composed of a sodium tungsten bronze. By using a sodium tungsten bronze, the potential between reference electrode and solid electrolyte is kept constant.

The invention will be described in greater detail below with reference to embodiments which will reveal further important features.

DESCRIPTION OF THE PREFERRED EMBODIMENTS

Figure 1:
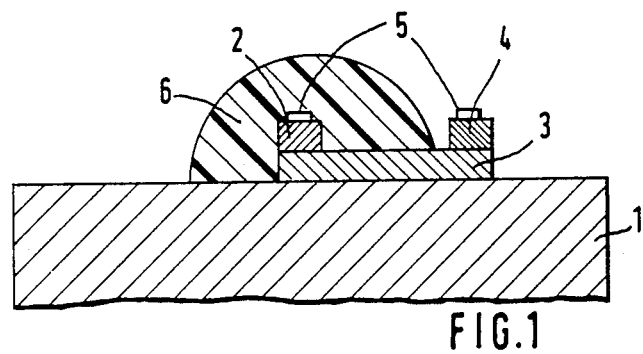
FIG. 1 is a schematic representation of a sensor made in accordance with the invention in a first embodiment in which the electrodes are in a planar arrangement.

The electrodes and the solid electrolyte are printed in thick-film technology in several process steps onto a commercially available substrate material 1, e.g. 96% $Al_2O_3$, in planar (FIG. 1) or transverse (FIG. 2) arrangement, namely a reference electrode 2, a solid electrolyte 3 and a detector electrode 4. Electrodes 2 and 4 are provided with conventional connecting leads or contacts 5. Detector electrode 4 may be composed, for example, of platinum, palladium or palladium oxide. Reference electrode 2 may be produced of materials exhibiting constant sodium ion activity, for example of a sodium tungsten bronze. After each printing process, the respective layer is sintered or fired or oxidized under defined conditions. In a last process step, after electrodes 2 and 4 have been contacted with connecting leads 5, solid electrolyte 3 and part of the surface of detector electrode 4 may be sealed by a covering 6 of glass or plastic.

An example of this manufacturing process includes: pressing the nasicon, heating at 120° C., 30 minutes in air; pressing of the electronic terminals (for example gold), heating at 950° C., 15 minutes in air; pressing of the platinum electrode, heating at 950° C., 15 minutes in air; pressing the tungsten bronze, heating at 750° C., 15 minutes in nitrogen; and pressing the glass cover paste, burning at 700° C., 15 minutes in nitrogen.

Figure 2:
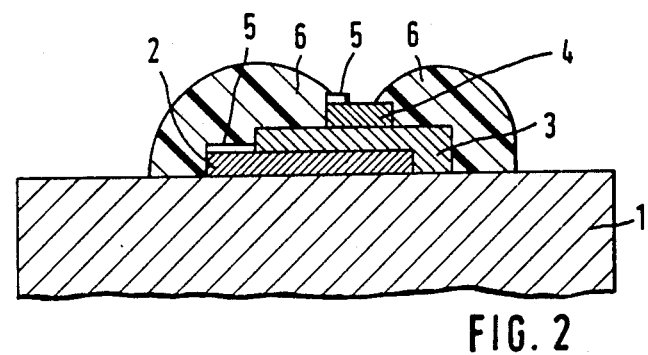
FIG. 2 is a schematic representation of another embodiment of the sensor made in accordance with the invention in which the electrodes are arranged transversely.
Figure 3:
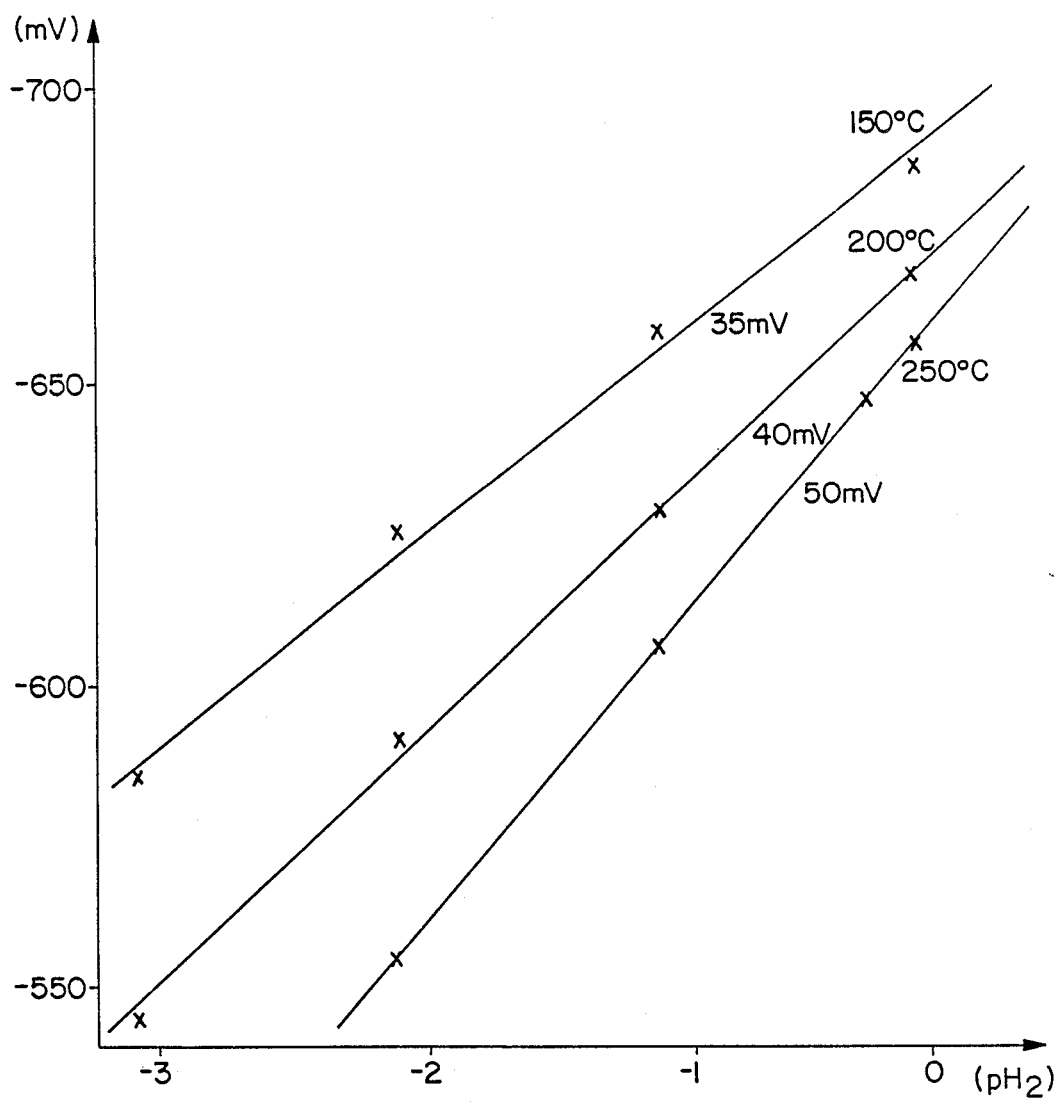
FIG. 3 is a graph showing the response in millivolts of a Nasicon $H_2$ sensor at three different temperatures, plotted against the hydrogen concentration of a hydrogen-nitrogen mixture.
Figure 4:
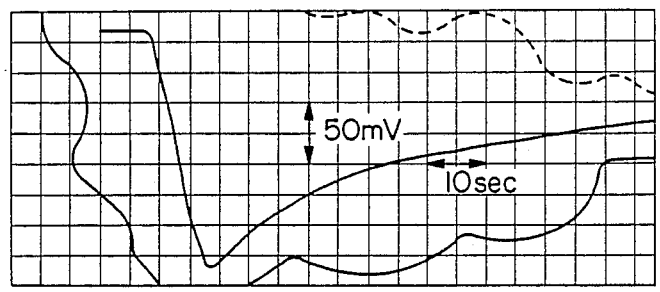
FIG. 4 shows the change in the sensor signal in air during the addition of 2% hydrogen.

The cover may seal the reference electrode and part of the solid electrolyte, leaving the detector electrode uncovered, as in FIG. 1. Another possibility as shown in FIG. 2 is that the cover may seal substantially all of the sensor not protected by the substrate, but exposing part of the detector electrode.

The starting materials for the electrodes may be commercially available platinum or palladium pastes. A printing paste for the solid electrolyte is obtained if, for example, nasicon electrolyte powder is mixed in the correct ratio with a vehicle suitable for thick-film pastes, e.g. ethyl cellulose and terpineol. The nasicon electrolyte powder is produced, for example, by sintering of powder mixtures and subsequent grinding or using a sol-gel process.

Commercially available cover materials (silicone, lacquers) or printed layers of commercially available dielectric pastes or cover glass pastes are suitable as covers.

The solid electrolyte of nasicon has the chemical formula $$Na_{1+x}Zr_2Si_xP_{3-x}O_{12}, \text{ where } 0 \leq x \leq 3.$$

In tests, $x=2.2$ and $x=2$ were used and these tests produced good results.

It can thus be seen that the electrochemical reaction between the hydrogen gas to be detected and the sensor according to the present invention causes the latter to react very quickly and to emit a signal via its connecting lead after a short response time, with such signal then being processed further, possibly in a subsequently connected electronic system likewise produced in thick-film technology. (High impedance amplifier, level detector).

The present disclosure relates to the subject matter disclosed by the patent issued in the Federal Republic of Germany, P 36 39 802.0, on Nov. 21st 1986, the entire specification of which is incorporated herein by reference.

It will be understood by those of ordinary skill in the art that the above description of the present invention is susceptible to various modifications, changes and adaptations, which are intended to be comprehended within the meaning and range of equivalents of the appended claims.

What is claimed is:

1. A method for making a sensor for monitoring hydrogen concentrations in gases, comprising the steps of:
    printing a thick film solid electrolyte body comprising at least one of nasicon, titsicon, khibinskite, wadeite and $\beta$-Al$_2$O$_3$ onto a substrate;
    printing a thick film detector electrode comprising one of a metal or metal oxide selected from the group consisting of platinum, platinum oxide, palladium, and palladium oxide and having a surface to be exposed to a gas to be monitored onto said solid electrolyte body;
    printing a thick film reference electrode comprising sodium tungsten bronze onto said solid electrolyte body; and
    covering said reference electrode with an insulating material.

2. The method of claim 1, wherein said reference electrode is printed by pressing a sodium tungsten bronze paste and heating said sodium tungsten bronze paste at about 750° C. for about 15 minutes in nitrogen.

3. The method of claim 1, wherein said solid electrolyte comprises nasicon and said solid electrolyte is printed by pressing nasicon paste and sintering said nasicon paste at about 120° C. for about 30 minutes in air.

4. The method of claim 1, wherein said sensor includes an electronic terminal of gold and said electronic terminal is printed by pressing the gold and sintering the gold at about 950° C. for about 15 minutes in air.

5. The method of claim 1, wherein said insulating material comprises glass and said insulating material is applied to said reference electrode by pressing a glass cover paste and sintering said glass cover paste at about 700° C. for about 15 minutes in nitrogen.

6. The method of claim 1, wherein said electrolyte body comprises nasicon.

7. The method of claim 6, wherein said reference electrode comprises sodium tungsten bronze and said reference electrode is printed by pressing a sodium tungsten bronze paste and sintering said sodium tungsten bronze paste at about 750° C. for about 15 minutes in nitrogen.

8. The method of claim 1, wherein said electrolyte body comprises titsicon.

9. The method of claim 1, wherein said electrolyte body comprises khibinskite.

10. The method of claim 1, wherein said electrolyte body comprises wadeite.

11. The method of claim 1, wherein said electrolyte body comprises $\beta$-Al$_2$O$_3$.

* * * * *